United States Patent [19]
Crook

[11] Patent Number: 5,365,996
[45] Date of Patent: Nov. 22, 1994

[54] METHOD AND APPARATUS FOR MAKING CUSTOMIZED FIXATION DEVICES

[75] Inventor: David F. Crook, Garland, Tex.
[73] Assignee: Amei Technologies Inc., Wilmington, Del.
[21] Appl. No.: 896,595
[22] Filed: Jun. 10, 1992
[51] Int. Cl.$^5$ ............. G06F 15/42; B29C 35/08; B22C 7/02
[52] U.S. Cl. ............ 164/45; 164/35; 164/4.1; 364/413.13; 364/413.15; 364/474.05; 364/474.24; 128/653.1; 128/653.2; 264/22
[58] Field of Search ........... 164/34, 35, 45, 4.1, 164/150; 364/413.13, 413.15, 368, 474.05, 474.24; 128/653.1, 653.2; 264/22; 623/901, 17

[56] References Cited

U.S. PATENT DOCUMENTS

| | | | |
|---|---|---|---|
| 4,436,684 | 3/1984 | White | 264/138 |
| 4,729,098 | 3/1988 | Cline et al. | 364/414 |
| 4,760,548 | 7/1988 | Baker et al. | 364/718 |
| 4,827,413 | 5/1989 | Baldwin et al. | 364/413.19 |
| 4,841,975 | 6/1989 | Woolson | 128/653 |
| 4,876,509 | 10/1989 | Perlmutter | 324/309 |
| 4,912,659 | 3/1990 | Liang | 364/521 |
| 4,939,646 | 7/1990 | Essinger et al. | 364/413 |
| 4,940,412 | 7/1990 | Blumenthal | 623/901 |
| 4,976,737 | 12/1990 | Leake | 623/16 |
| 5,007,936 | 4/1991 | Woolson | 623/23 |
| 5,027,281 | 6/1991 | Rekow et al. | 364/474.24 |
| 5,059,359 | 10/1991 | Hull et al. | 264/22 |
| 5,063,375 | 11/1991 | Lien et al. | 340/703 |
| 5,104,592 | 4/1992 | Hull et al. | 264/22 |
| 5,173,220 | 12/1992 | Reiff et al. | 264/22 |
| 5,184,306 | 2/1993 | Erdman et al. | 364/474.05 |
| 5,218,427 | 6/1993 | Koch | 364/561 |

FOREIGN PATENT DOCUMENTS

| | | |
|---|---|---|
| 0093869 | 11/1983 | European Pat. Off. |
| 0097001 | 12/1983 | European Pat. Off. |
| 3522196 | 2/1986 | Germany |
| 9107139 | 5/1991 | WIPO |

OTHER PUBLICATIONS

Rhode, M. L. et al., "An Application of Computer Graphics and Networks to Anatomic Model and Prosthesis Manufacturing", *IEEE*, 1987 pp. 12–25.
Gordon, Dan and Udupa, J. K. "Fast Surface Tracking in Three-Dimensional Binary Images" *Computer Vision, Graphics, and Image Processing*, Feb. 1989 pp. 196–214.
Cook, P. N. "A Study of Three-Dimensional Reconstruction Algorithms" 1981 *Automedica*, vol. 4 pp. 3–12.
"The Display of 3-Dimensional Anatomy with Stereolithographic Models", N. J. Mankovich, A. M. Cheeseman and N. G. Stoker, *Journal of Digital Imaging*, vol. 3, No. 3, Aug. 1990, pp. 200–203.
"Two Algorithms for the Three-Dimensional Reconstruction of Tomograms", H. E. Cline, W. E. Lorensen, S. Ludke, C. R. Crawford and B. C. Teeter, *Medical Physics*, May–Jun. 1988, pp. 320–327.
"3D Imaging in Medicine", J. K. Udupa and G. T. Herman, *CRC Press*, 1991.
"Fertigung Von Knochenmodellen Nach Computer-Tomographie-Daten Zur Verwendung in Chirurgie und Orthopaedie" G. Giebel et al. *Biomedizinische Technik*, vol. 30, No. 5, 1985, pp. 111–114.
"Three Dimensional Computed Tomography for Maxillofacial Surgery: Report of Cases", William C. Donlon, Perry Young and Art Vassiliadis, *Journal of Oral and Maxillofacial Surgery*, vol. 46, No. 2, Feb. 1988, pp. 142–147.

*Primary Examiner*—P. Austin Bradley
*Assistant Examiner*—Erik R. Puknys
*Attorney, Agent, or Firm*—Baker & Botts

[57] ABSTRACT

A method and apparatus is described for making a custom fixation device. The apparatus comprises a means for scanning a treatment site and for producing image data representative of the treatment site. A means for generating a set of vectors is included for defining a set of points, the set of vectors representative of the treatment site, the points associated with a surface, part of the surface representative of part of the treatment site, part of the surface hidden from view. Further, means for associating each point with a pole of a control polygon of a non-uniform rational B-spline, means responsive to the non-uniform rational B-spline for constructing a model of the treatment site, and means responsive to the model for constructing the fixation device are described.

15 Claims, 5 Drawing Sheets

METHOD AND APPARATUS FOR MAKING CUSTOMIZED FIXATION DEVICES

CROSS-REFERENCE TO RELATED APPLICATIONS

This application is related to U.S. application Ser. No. 08/158,732 filed Nov. 29, 1993 by David F. Crook and entitled "Method For Representing a Patient's Site as Data For Use With a CAD or CAM Device", pending, which is a continuation of application Ser. No. 07/896,597 filed Jun. 10, 1992 by David F. Crook and entitled "Method For Representing a Patient's Treatment Site As Data For Use With a CAD or CAM Device", now abandoned.

TECHNICAL FIELD OF THE INVENTION

This invention relates generally to the field of medical fixation devices and more specifically to a method and apparatus for making customized fixation devices.

BACKGROUND OF THE INVENTION

A fixation device is commonly used by the medical profession to provide correct settings for bones that have become injured or malformed either due to illness or injury. Typically, a surgeon operates on the patient to expose the damaged bone or structure such as a hip joint or spinal column, perform the necessary corrective surgery and install a traditional fixation device using standard components that need to be adjusted once attached to the patient. These traditional devices are difficult if not impossible to customize for individual patients and individual medical conditions prior to surgery.

A need has arisen for a new method and apparatus for making customized fixation devices that would be individualized for each patient and each medical condition being treated prior to the actual surgery. Such a device would dramatically shorten the amount of time necessary for operating on the patient as well as provide a better, more individualized, fixation device to particularly account for the abnormality being treated.

One approach to this problem has been to take data derived from a Computerized Axial Tomography (CAT) scan and using that data in combination with data derived from a Computer Aided Design (CAD) system to customize a hip prosthesis. In this prior art device, a CAT scan of the patient's hip is used in connection with the CAD system to mill by hand a standard stem that matches the inner canal of the patient's hip. While this approach has achieved some of the aforementioned advantages, it has significant disadvantages making it generally unacceptable to widespread use outside the area of hip prosthesis.

SUMMARY OF THE INVENTION

The apparatus of the present invention overcomes the disadvantages of the prior art and provides a unique device for making customized fixation devices.

A method and apparatus is described for making a custom fixation device. The apparatus comprises a means for scanning a treatment site and for producing image data representative of the treatment site. A means for generating a set of vectors is included for defining a set of points, the set of vectors representative of the treatment site, the points associated with a surface, part of the surface representative of part of the treatment site, part of the surface hidden from view. Further, means for associating each point with a pole of a control polygon of a non-uniform rational B-spline, means responsive to the non-uniform rational B-spline for constructing a model of the treatment site, and means responsive to the model for constructing the fixation device are described.

A technical advantage of the present invention is that a custom contoured fixation device can be provided that employs lower profile components using pre-aligned and pre-determinated holes.

Another technical advantage of the present invention is that the position of optimum stabilization can be determined via electronic surgery.

Another technical advantage of the present invention is that depth and orientation for placing the fixation device is determined prior to the surgery and the surface contouring can be used to reduce high stress in the bone avoiding the need for sublaminar wires.

BRIEF DESCRIPTION OF THE DRAWINGS

For a more complete understanding of the present invention and the advantages thereof, reference is now made to the following description taken in conjunction with the accompanying drawings, in which.

DETAILED DESCRIPTION OF THE PREFERRED EMBODIMENT

Figure 1:
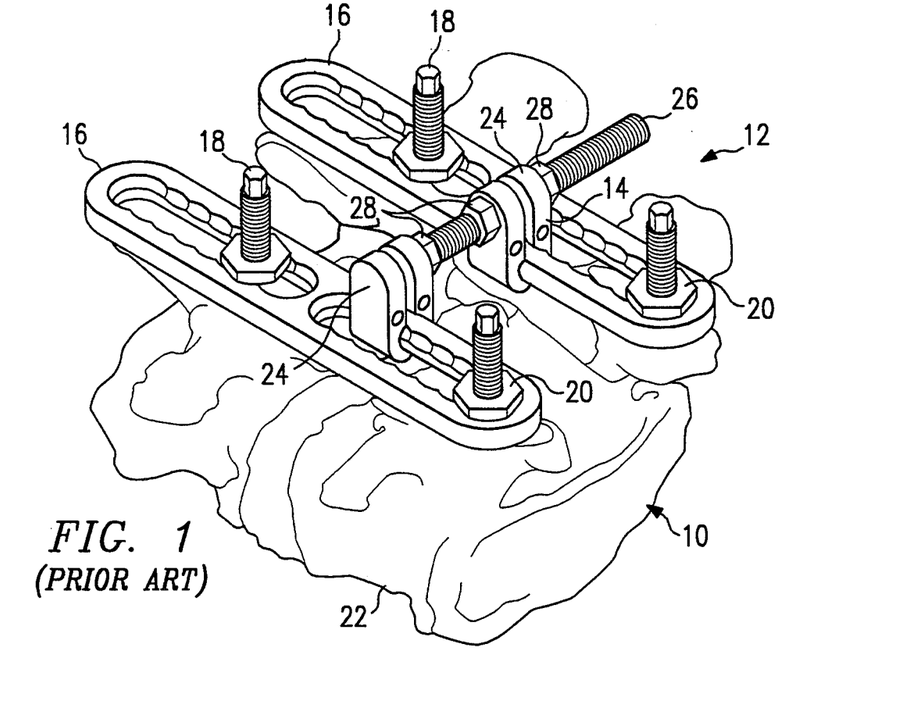
FIG. 1 depicts a traditional fixation device.

FIG. 1 depicts a treatment site 10 outfitted with a traditional fixation device 12. The traditional fixation device 12 comprises cross-bracing assembly 14, plates 16 and screws 18. Each of the items that comprises the traditional fixation device needs to be of a generalized nature as the surgeon does not have the ability to customize the device prior to surgery. As a result, the traditional fixation device 12 has a number of sharp edges and raised portions that can both be points of irritation as well as sources of infection. Each of screws 18 has a locking nut 20 to fasten the respective plate 16 to bone 22 of treatment site 10. Cross-bracing assembly 14 has clamps 24 that are held together using bolt 26 and nuts 28.

Figure 2:
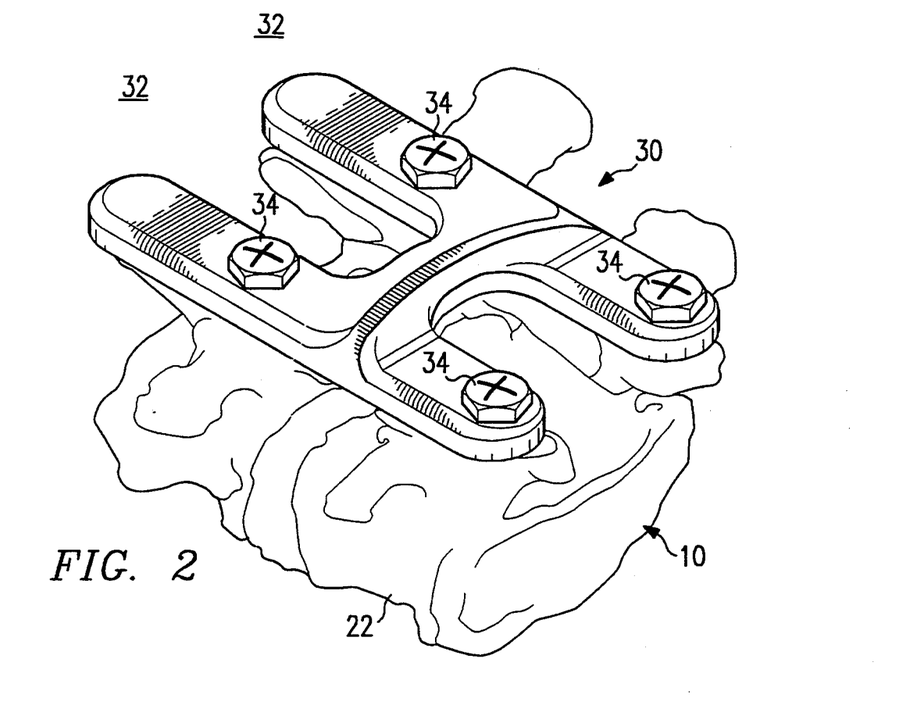
FIG. 2 depicts a customized fixation device made in accordance with the present invention.

In contrast, FIG. 2 shows a treatment site 10 using a customized fixation device 30 made prior to surgery in accordance with the teachings of this invention. Because customized fixation device 30 can be manufactured prior to the surgery, it is designed specifically for the particular patient and is configured to conform as close as possible to the treatment site. As a result, the profile of device 30 is lower, all sharp edges are substantially reduced and the need for general types of assemblies such as plates and clamps are eliminated. Referring to FIG. 2, fixation device 30 comprises a single contoured brace 32 fastened to bone 22 using low profile screws 34. The edges of device 30 are rounded. Thus, potential sources of irritation and infection are reduced.

Figure 3:
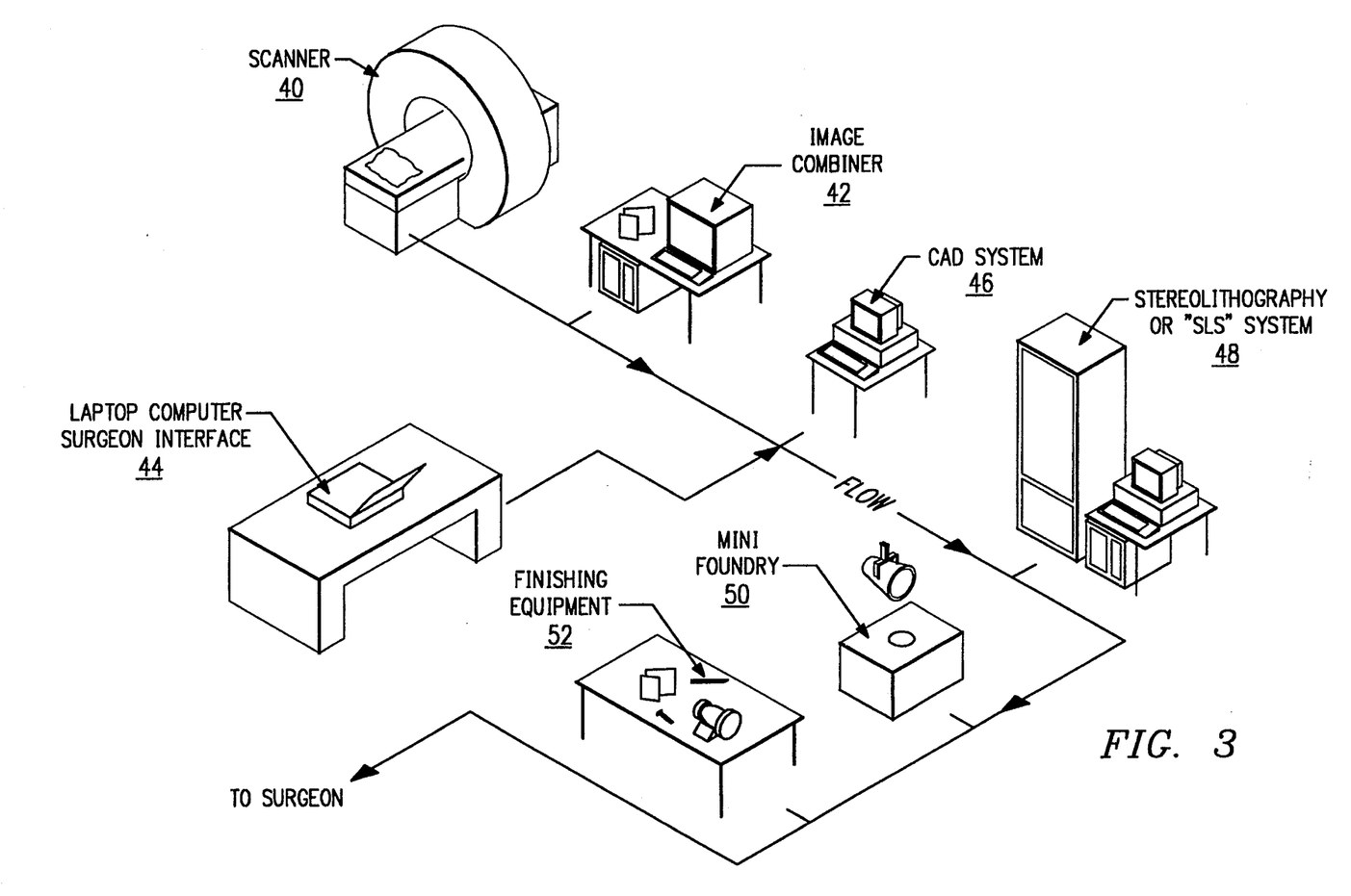
FIG. 3 shows an apparatus made in accord with the present invention.

Referring now to FIG. 3, an apparatus for making a custom fixation device is shown. The apparatus comprises a scanning apparatus 40, an image combiner 42, a surgeon interface computer 44, a CAD system 46, a stereolithography system ("SLS") 48, a mini foundry 50 and finishing equipment 52.

It is contemplated by the present invention that a patient undergoing surgery will have a tomographic scan of the treatment site. Scanning apparatus 40 generates tomographic image data representative of a treatment site near in time and prior to the corrective procedure. The scanner will generate image data, as is more fully described below, that provides a series of two-dimensional images of the treatment site taken from various perspectives and orientations. The image data is then generally stored on disk or magnetic tape or other mass computer storage that can be provided to an image combiner 42.

Image combiner 42 or imaging system 42 takes the raw tomographic data and modifies it so that it will be suitable for use in the CAD system 46. Image combiner 42 is connected to surgeon interface computer 44.

Surgeon interface computer 44 permits the surgeon or other medical professional to review the tomographic image data and manipulate it in any fashion. Surgeon interface computer 44 is a conventional digital computer such as a lap-top personal computer that interacts with the conventional image combiner software as is known to those well skilled in the art. The modified image data, if modification is so desired, is then converted to CAD system data and loaded on to a conventional CAD system 46.

CAD system 46 is provided with the two-dimensional rendition of a three-dimensional treatment site suitable for the design of the customized fixation device. A technician or other suitably trained medical engineering professional using a library of components customizes a specific fixation device for use on the specified treatment site. Once the customized fixation device design is completed on CAD system 46, the CAD data is converted to slice data using a conventional digital computer suitably programmed, as is well known to those skilled in the art, to provide input to a stereolithography system 48.

Stereolithography system 48 takes the two-dimensional slice data and generates a three-dimensional object. The data contained in the CAD system 46 includes both data representing the treatment site as well as data showing the customized fixation device. Using stereolithography system 48, models of both the fixation device and the treatment site can be produced.

Once the treatment site and the fixation device have been rendered into three-dimensional objects using stereolithography system 48, the three-dimensional model of the treatment site can be provided to the surgeon for use in determining the appropriate surgical technique. The customized fixation device can also be provided to a mini-foundry 50 for producing a metal part using the lost wax technique as is well known to those skilled in the art. The customized fixation device is made out of surgical steels, suitable for implantation as is conventionally known. Once the part is cast, it is provided to finishing equipment 52 for final preparation, such as cleaning, polishing and packaging, before sterilization and implantation by the surgeon.

SLS 48 may produce three-dimensional objects such as a custom prosthetic device and a drill guide. The former object is depicted in FIG. 2. The later object might appear as the former but the holes for screws 34 would be aligned such that a drill bit would bore a socket through the holes and into treatment site 10 along a preselected axis. In both cases, the device is fabricated with a contoured face that mates with treatment site 10.

Figure 4:
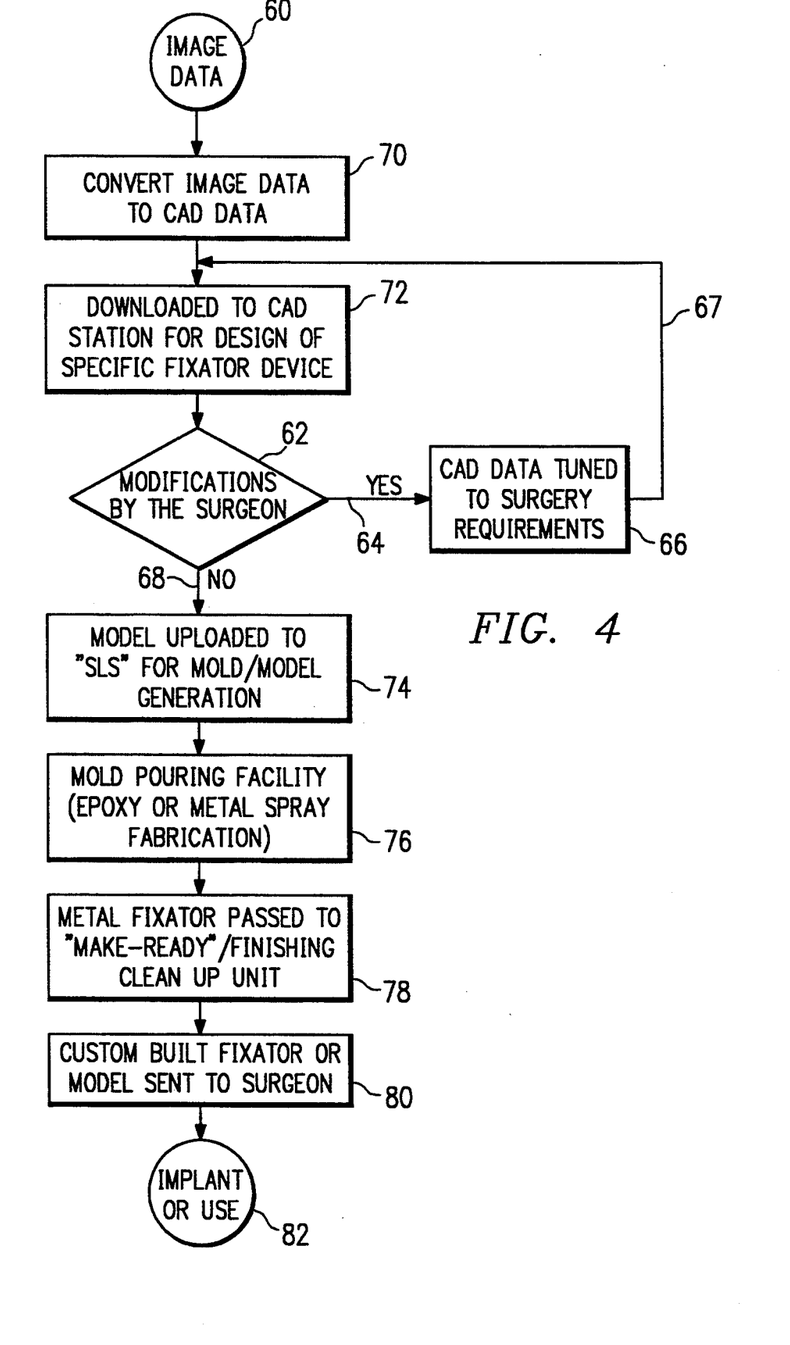
FIG. 4 is a block diagram describing one process sequence of the disclosed invention.

Referring now to FIG. 4, a flow chart is depicted showing a method for making, for instance, a customized fixation device. The process begins at step 60 where tomographic image data is provided, typically on computer tape. First, the image data is converted in block 70 to CAD data. Block 70 is further described below in connection with FIG. 11. At a block 72, the CAD data is downloaded to a CAD workstation for design of the customized fixation device around the three-dimensional rendering of the patient treatment sight. At decision point 62, the process branches depending on whether the CAD data requires modification by the surgeon. If the answer is yes, the process follows path 64 where at a box 66, the CAD data is tuned to the surgical requirements of the surgeon. The surgeon may, for instance, isolate the area of interest for later processing steps. Then following path 67, the modified CAD data is returned to the CAD station. The loop going through box 66 will continue until such time as the surgeon is satisfied that the data conforms with his or her needs. At a block 74, the CAD image of either the customized fixation device or the treatment site, or both, are uploaded to a stereolithography system after the CAD data has been converted to slice data suitable for a stereolithography system.

At a block 74, the stereolithography system generates a model of either the fixation device or treatment site or both. After a three-dimensional model has been rendered in block 74, a mold pouring facility, such as a minifoundry, is used to fabricate a solid metal device suitable for implantation at block 76. At a block 78, the metal fixation device is made ready for implantation and finished by removing all rough edges, burrs, machining marks, etc. A device with smooth rounded edges is thereby provided to the surgeon to minimize the possibility of irritation and infection in the patient. At a block 80, the customized fixation device may be assembled with a model of the treatment site for approval by the surgeon. The surgeon, if satisfied, implants the custom device into the patient at a block 82.

Medical tomographic imaging devices such as CT scanners, magnetic resonance imaging ("MRI") scanners and x-ray machines sample certain properties of tissue within a region of the human body. CT and MRI scanners sample the property within a two-dimensional plane. X-ray machines condense the property of several overlapping planes into a single two-dimensional plane. CT and MRI scanners then represent the sampled values as one or as a set of cross-sectional images.

The sampled property of a MRI scanner is the magnetic moment of a proton. The magnetic moment indicates the number of protons at the location and hence the overall mass density at the point. CT scanners and x-ray machines measure the macroscopic cross-section, Σ, of a sample at the operating frequency of the CT scanner or x-ray machine. The macroscopic cross-section is proportional to the atomic density of the sample and, hence, may be used as a measure of the sample's local density.

Using either method, the measured density may be used to determine the boundaries between internal body structures if the accuracy and resolution of the measuring systems is sufficiently high. Present CT and MRI scanners are able to resolve volumes ("voxels," typically rectangular boxes each of whose six sides are rectangles) having dimensions $0.1 \times 0.1 \times 1.5$ mm. This is sufficiently high to differentiate the delicate bony structures of the cranium and the intricate soft structures of the brain.

Other known tomographic methods such as positron emission ("PET") and ultrasound radiation techniques may be used to generate suitable data for the disclosed method.

CAD systems model some, if not all, shapes and structures as non-uniform rational B-splines ("NURBS"). NURBS have the advantage of allowing free-form as well as regular geometric shapes to be modeled and manipulated easily by a computer. NURBS do this by using multiple low order equations which require less computing power than would fewer higher order equations.

B-spline curves or surfaces are shapes comprising many polynomial segments pieced together. The order of the polynomials may be set by an operator to globally shape the curve. For instance, the segments may have order "one" which results in a series of straight segments. An order greater than one results in a series of curved segments. NURBS have the property that they are smooth at the junction between adjacent segments.

B-spline curves are defined by a set of poles, by a set of knots, and by a control polygon. A B-spline curve has a pole at each endpoint and a variable number spaced throughout the curve space. Each pole influences the shape of the curve by steering the curve toward them. The effect of each pole on the shape of the curve is determined by a set of blending functions associated with each pole. These blending functions make the curve smooth or straight. If a B-spline curve is non-uniform, the spacing between poles may vary from pole to pole. The control polygon is a polygon having each of its vertices coincident with one of the poles. It may be open like a zig-zag line or closed like a square. A knot is a point, usually operator selected, which defines where one polynomial segment ends and another begins. This allows discontinuities to exist in the generated surface.

Figure 5:
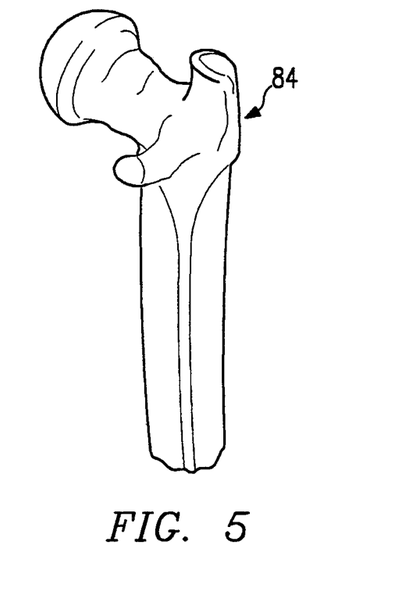
FIG. 5 depicts an isometric view of a human femur.

FIG. 5 depicts an isometric view of a human femur 84. Although femur 84 is depicted devoid of surrounding tissue, it should be understood that femur 84 is, in the normal practice of the disclosed invention, hidden from view by surrounding tissue. In the illustration described herein, the importance of the shape of femur 84 is assumed. For instance, it may be necessary to replace the hip joint of femur 84 due to a pathological condition.

Figure 6:
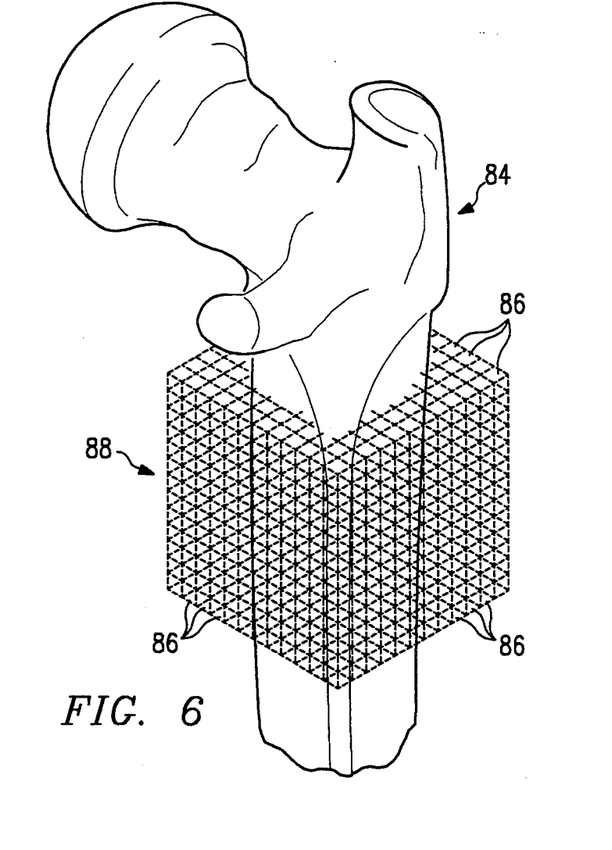
FIG. 6 is a graphical representation of a scanned volume partially coincident with the femur depicted in FIG. 5.

FIG. 6 is a graphical representation of a scanned volume partially coincident with the femur 84 depicted in FIG. 5. Femur 84 is scanned by a suitable imaging system such as a CT or MRI scanning system (not shown). The scanning system will determine the density of each voxel 86 in a region of interest indicated generally at 88. Although voxels 86 are depicted as cubes, other geometries including cylindrical, may be appropriate depending upon the selected scanning system. Also, voxels 86, though cubical as depicted, may have one or two dimensions substantially greater than the other. For instance, voxels 86 may have a thickness approximately ten times greater than their length or width. Such a variation is caused by the scanning nature of CT and MRI technologies. These scanners "slice" a subject into a series of parallel planes. The resolution of the scanners along the axis perpendicular to the series of planes may be less than the resolution within the planes.

Figure 7A:
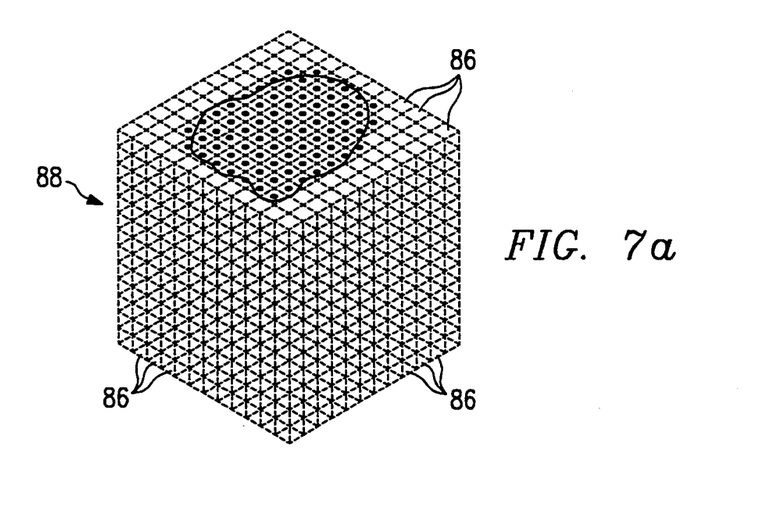
FIGS. 7a and 7b are graphical representations of the scanned volume of FIG. 6.
Figure 7B:
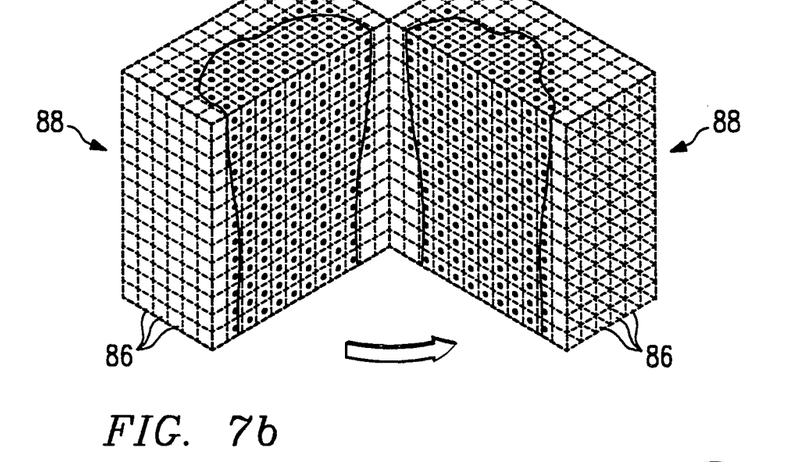

FIGS. 7a and 7b are graphical representations of the scanned region of interest 88 of FIG. 6. After scanning, each voxel has a density associated with it. These densities may be filtered according to known methods to produce a binary density. Binary density is one in which each voxel density is either 0 or 1. Those voxels corresponding to a volume of space having a density greater than a preset threshold are assigned a density of one and are indicated by a dot. Those voxels having a density less than the threshold are assigned a density of zero and are indicated by a blank voxel. Only those voxels on the front three faces are depicted in FIG. 7a. FIG. 7b depicts the scanned volume split in half along a vertical plane. The right half of the volume has been rotated counterclockwise 90° and has been translated to the right rear for illustrative purposes. An internal portion of each scanned slice is therefore visible. The outline of the femur 84 from FIG. 6 is also depicted as it is coincident with each voxel by a solid line.

The voxels 86 which correspond to femur 84 may be determined by other means. For instance, the voxels which correspond to femur 84 may be determined by a boundary based approach. A boundary based approach is one which examines density variation as a function of position to produce a density gradient at each voxel. Voxels having a gradient greater than a preset limit indicate that the voxel corresponds to the boundary of femur 84. Voxels within a structure may also be distinguished from those outside the structure by their common features or properties. For instance, if it was known a priori that the scanned structure comprised a first and second region having a corresponding first and second density, each voxel could be allocated to either group depending upon its particular density. These latter two methods and the binary filtering method each generate a set of voxels corresponding to femur 84.

Figure 8:
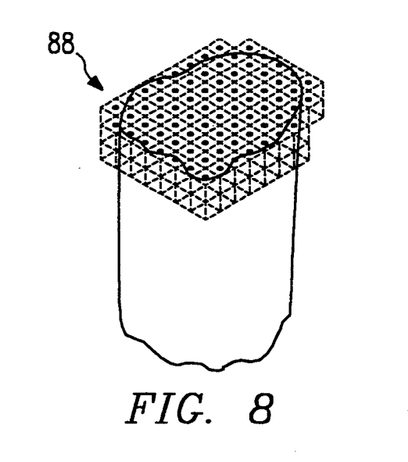
FIG. 8 is a further graphical representation of the scanned volume of FIG. 6.

FIG. 8 is a further graphical representation of the scanned volume of FIG. 6. Here, all voxels not corresponding to femur 84 have been removed. In addition, only the upper two most layers of voxels are depicted for clarity. The underlying bone mass is depicted isometrically by solid lines.

Figure 9:
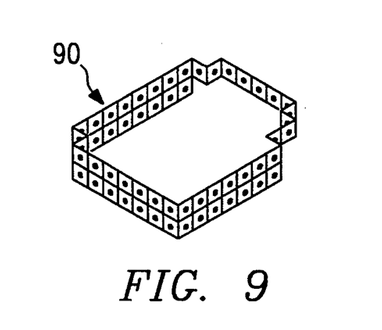
FIG. 9 is a further graphical representation of the scanned volume of FIG. 6.

FIG. 9 is a graphical representation of a surface 90 generated by the scanned volume depicted in FIG. 8. After the voxels corresponding to the scanned structure have been identified, a surface is extracted corresponding to or defining the surface of the underlying scanned structure. The surface may be extracted according to the known method of Surface Tracking. Here, the surface corresponding to the first two layers of voxels is depicted. The surface corresponding to the plane which bisects femur 84 perpendicular to its length is omitted for clarity and because it is an arbitrary starting surface.

The surface is then mathematically described as a set of vectors to each surface of a boundary voxel. The particular transformation from CT slice location to vector depends upon the coordinate system of the underlying CT data. For instance, an MRI scan in rectangular coordinates (x, y, z) may be transformed to a vector in a rectangular coordinate system by scaling the triplet of numbers by three scaler quantities corresponding to an absolute or relative size. A CT scan in cylindrical coordinates may require a different transformation. All non-surface data from the original CT scan may then be discarded. The remaining data need not be stored in the original array format (an N×M array for each slice). The vectors may simply be stored as a table of triplets of numbers. This reduction allows substantial memory savings.

Figure 10:
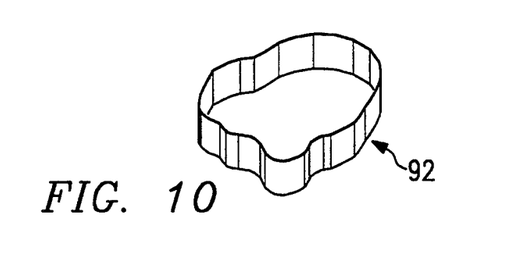
FIG. 10 is an isometric view of the CAD surface generated from FIG. 6.

FIG. 10 is an isometric view of the CAD surface 92 generated from FIG. 6. According to the disclosed invention, each vector data point determined in connection with FIG. 6 is identified as a control point or pole of a NURB surface to a CAD system. A CAD system will then generate a series of low order polynomial equations which approximate the input data. The CAD processor will perform operations on these equations rather than on the input vector data points. The number of vectors or points may be further reduced by known geometric techniques. This increases processing speed and reduces memory requirements a second time.

Figure 11:
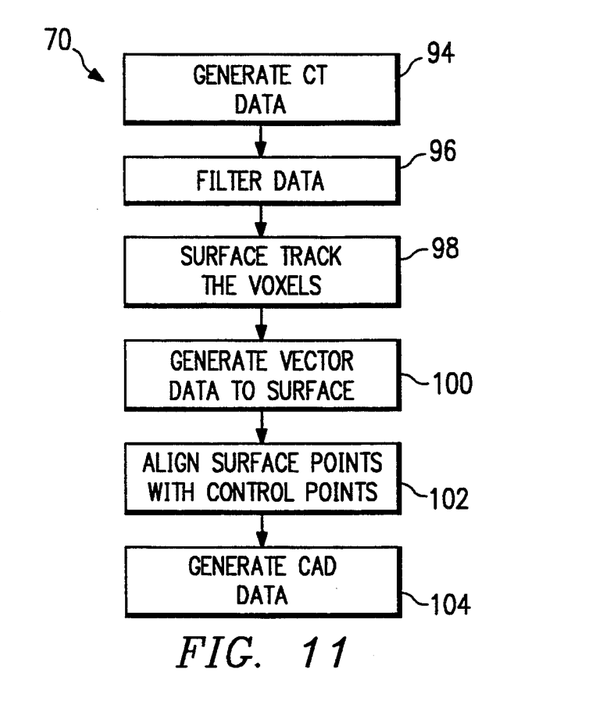
FIG. 11 is a block diagram describing one process sequence of the disclosed invention.

FIG. 11 is a block diagram further describing block 70 of FIG. 4. CT data is generated in a block 94 as a series of sequential two-dimensional data arrays described above. The raw data is typically acquired using tomographic techniques. However, other methods may generate suitable data for the disclosed invention. The raw data is then filtered in a block 96 to distinguish between those data points corresponding to a particular structure of interest and those data points corresponding to other structures. The filtered data is then analyzed to produce a surface of the interested structure in a block 98. As described above, the method of surface tracking is used in the preferred embodiment. Other methods, however, may be used in place of this method. The surface is used to generate a set of vector data points corresponding to each voxel situated at a boundary of the structure of interest in a block 100. These data points are then fed to a CAD system with an instruction to treat each data point as a pole of a non-uniform rational B-spline in a block 102. The CAD system then generates a mathematical formula which approximates the surface points in a block 104.

The CT data may be generated by a suitable system such as a GE 9800 Scanner available from General Electric Corporation coupled to an imaging system such as one offered by Surgicad Corporation of Lebanon, N.H. The CAD data may be generated on a microcomputer or on a dedicated work station such as an Intergraph Engineering Modeling System from Intergraph Corp., of Huntsville, Ala. The remaining steps, blocks 96 through 102, may be performed by the Surgicad or Intergraph systems or by a suitable standalone microcomputer having a compatible data storage/retrieval system with both the imaging and CAD systems. The plastic implant model may be fabricated on a SLA250 manufactured by 3D Systems of Valencia, Calif.

Although the present invention and its advantages have been described in detail, it should be understood that various changes, substitutions and alterations can be made herein without departing from the spirit and scope of the invention as defined by the appended claims.

What is claimed is:

1. An apparatus for making a custom fixation device comprising:
    means for scanning a treatment site and for producing image data representative of the treatment site;
    means for generating a set of vectors defining a set of points, the set of vectors representative of the treatment site, the points associated with a surface, part of the surface representative of part of the treatment site, part of the surface hidden from view;
    means for associating each point with a pole of a control polygon of a non-uniform rational B-spline;
    means responsive to the non-uniform rational B-spline for constructing a model of the treatment site; and
    means responsive to the model for constructing the fixation device.

2. The apparatus of claim 1 wherein said means for scanning is a computerized axial tomography device.

3. The apparatus of claim 1 wherein said set of vectors are used by a computer aided design device.

4. The apparatus of claim 1 wherein said fixation device constructing means is a stereolithographic device.

5. A method for constructing a customized fixation device comprising:
    scanning a treatment site to produce image data representative of the treatment site;
    receiving a plurality of sets of data values, the data values within each set corresponding to a property of the treatment site along a first and second dimension, each set corresponding to the value at a predetermined position along a third dimension;
    generating a set of points from the sets of data values, the points defining a surface, part of the surface representative of the treatment site;
    generating a vector to each point;
    associating each vector with a pole of a control polygon of a non-uniform rational B-spline;
    generating a model of the treatment site in accordance with the control polygon; and
    constructing a customized fixation device in accordance with the model.

6. The method of claim 5, further comprising the step of manipulating the image data prior to said step of generating a model.

7. The method of claim 5, wherein said model of the treatment site is formed in three dimensions.

8. An apparatus for making customized fixation devices comprising:
    means for generating image data representative of a treatment site;
    means for modifying the image data;
    means for generating from the image data a set of points associated with a surface, part of the surface representative of the treatment site, part of the surface hidden from view;
    means for generating a set of vectors associated with the points;
    means for associating each vector with a pole of a control polygon of a non-uniform rational B-spline;
    means for translating the non-uniform rational B-spline into slice data suitable for use with a stereolithographic system; and
    means for converting the slice data to a three dimensional object representative of a treatment site.

9. The apparatus of claim 8, wherein the means for generating image data is a CAT scanner.

10. The apparatus of claim 8, wherein the means for generating image data is an MRI scanner.

11. The apparatus of claim 8, wherein the means for modifying said image data is a computer.

12. The apparatus of claim 8, wherein the means for associating is a computer.

13. The apparatus of claim 8, wherein the means for translating is a computer.

14. The apparatus of claim 8, wherein the means for converting is a stereolithographic apparatus.

15. The apparatus of claim 8, further comprising a local area network connecting the means for modifying, the means for associating and the means for translating.

* * * * *